(12) United States Patent
Xie et al.

(10) Patent No.: US 11,536,611 B2
(45) Date of Patent: Dec. 27, 2022

(54) TEMPERATURE MEASURING DEVICE AND TEMPERATURE MEASURING METHOD FOR MEASURING TEMPERATURE OF MOLTEN METALS

(71) Applicant: SHENYANG TACO BLUE-TECH CO., LTD., Shenyang (CN)

(72) Inventors: Qixian Xie, Shenyang (CN); Jiu Zhang, Shenyang (CN); Guohui Mei, Shenyang (CN); Bin Liang, Shenyang (CN); Jie Sun, Shenyang (CN)

(73) Assignee: Shenyang Taco Blue-Tech Co., Ltd., Liaoning (CN)

( * ) Notice: Subject to any disclaimer, the term of this patent is extended or adjusted under 35 U.S.C. 154(b) by 438 days.

(21) Appl. No.: 16/627,666

(22) PCT Filed: Jun. 30, 2017

(86) PCT No.: PCT/CN2017/091121
§ 371 (c)(1),
(2) Date: Dec. 30, 2019

(87) PCT Pub. No.: WO2019/000402
PCT Pub. Date: Jan. 3, 2019

(65) Prior Publication Data
US 2020/0158575 A1     May 21, 2020

(51) Int. Cl.
*G01J 5/00* (2022.01)
*G01K 1/12* (2006.01)
(Continued)

(52) U.S. Cl.
CPC .............. *G01J 5/004* (2013.01); *B22D 2/006* (2013.01); *G01J 5/046* (2013.01); *G01J 5/0818* (2013.01);
(Continued)

(58) Field of Classification Search
CPC .......... G01J 5/004; G01J 5/046; G01J 5/0818; G01J 5/0887; G01N 33/205; B22D 2/006; G01K 1/125
See application file for complete search history.

(56) References Cited

U.S. PATENT DOCUMENTS 5,180,228 A    1/1993   Tarumi et al.
5,360,269 A * 11/1994   Ogawa .................. G01K 1/105
                                                    374/208
(Continued)

FOREIGN PATENT DOCUMENTS

| CN | 2513090 Y | 9/2002 |
| CN | 2729668 Y | 9/2005 |

(Continued)

OTHER PUBLICATIONS

Tao et al.—CN-205861217-U—Google Patents English obtained May 5, 2022 (Year: 2022).*

*Primary Examiner* — David P Porta
*Assistant Examiner* — Jeremy S Valentiner
(74) *Attorney, Agent, or Firm* — The Webb Law Firm (57) ABSTRACT

The disclosure includes a temperature measuring device and a temperature measuring method for measuring the temperature of molten metals. The temperature measuring device includes a temperature sensing element, a support tube, a connecting tube and an exhaust structure. The temperature sensing element is a cermet tube with a closed end and an open end, and can sense the temperature of a molten metal and emit stable thermal radiation energy based on the blackbody cavity principle when being extended into the molten metal. The open end of the cermet tube is fixedly connected to one end of the support tube, the cermet tube is communicated with the support tube, and the other end of the support tube is fixedly connected with the connecting
(Continued)

tube. The exhaust structure is used to discharge the smoke inside the cermet tube and the support tube.

14 Claims, 9 Drawing Sheets

(51) Int. Cl.
*B22D 2/00* (2006.01)
*G01N 33/205* (2019.01)
*G01J 5/04* (2006.01)
*G01J 5/0818* (2022.01)
*G01J 5/08* (2022.01)

(52) U.S. Cl.
CPC ............ *G01J 5/0887* (2013.01); *G01K 1/125* (2013.01); *G01N 33/205* (2019.01)

(56) References Cited

U.S. PATENT DOCUMENTS

| | | |
|---|---|---|
| 5,364,186 A | 11/1994 | Wang et al. |
| 6,846,105 B2 | 1/2005 | Xie et al. |
| 9,243,958 B2 | 1/2016 | Goda |
| 2015/0323258 A1 | 11/2015 | Neyens et al. |

FOREIGN PATENT DOCUMENTS

| | | | | |
|---|---|---|---|---|
| CN | 2729672 Y | | 9/2005 | |
| CN | 2852080 Y | | 12/2006 | |
| CN | 1936524 A | | 3/2007 | |
| CN | 102221408 A | | 10/2011 | |
| CN | 102998000 A | | 3/2013 | |
| CN | 204944679 U | | 1/2016 | |
| CN | 205049243 U | | 2/2016 | |
| CN | 205861217 U | | 1/2017 | |
| CN | 205861217 U | * | 1/2017 | ................ G01J 5/02 |
| CN | 206223302 U | | 6/2017 | |
| CN | 109590456 A | | 4/2019 | |
| DE | 19925685 A1 | * | 12/2000 | ............... B22D 2/00 |
| JP | S6080729 A | | 5/1985 | |
| JP | S62189629 U | * | 12/1987 | ............. G03B 15/06 |
| JP | H0238932 A | | 2/1990 | |
| JP | H0259629 A | | 2/1990 | |
| JP | 10197352 A | * | 7/1998 | ................ G01K 1/08 |
| KR | 20120033754 A | | 4/2012 | |
| TW | I561798 B | | 12/2016 | |
| WO | WO-9412870 A1 | * | 6/1994 | ............. B22F 7/002 |

* cited by examiner

TEMPERATURE MEASURING DEVICE AND TEMPERATURE MEASURING METHOD FOR MEASURING TEMPERATURE OF MOLTEN METALS

CROSS-REFERENCE TO RELATED APPLICATION

This application is the United States national phase of International Application No. PCT/CN2017/091121 filed Jun. 30, 2017, the disclosure of which is hereby incorporated by reference in its entirety.

Field of the Invention

The disclosure relates to the technical field of temperature measurement, in particular to a temperature measuring device and a temperature measuring method for measuring the temperature of molten metals.

BACKGROUND OF THE INVENTION

Description of Related Art

In the metallurgical industry, it is necessary to continuously measure the temperature of molten metals (such as molten steel and molten iron) in real time during production, which is of great significance to improve metal quality and production efficiency and reduce energy consumption.

Platinum rhodium thermocouples with protective tubes are usually used to measure the temperature of molten metals, in which the thermocouples are placed in the protective tubes, and then the protective tubes and the thermocouples inside are inserted into a molten metal to achieve continuous measurement of the temperature of the molten metal. This measurement cost much because of the high price of platinum rhodium thermocouples.

The United States Patent No. U.S. Pat. No. 6,846,105B2 discloses a method for continuous measurement of the temperature of molten steels and a temperature measuring tube which is composed of two tube bodies sleeved together with one end open and one end closed. When in use, the tube bodies are inserted into molten steel to a certain depth, and after thermal equilibrium is reached inside and outside the part of the tube inserted into molten steel, an isothermal blackbody cavity will be formed inside the part inserted into molten steel and the temperature of molten steel can be calculated by measuring the thermal radiation of the cavity with a thermometer.

Figure 1:
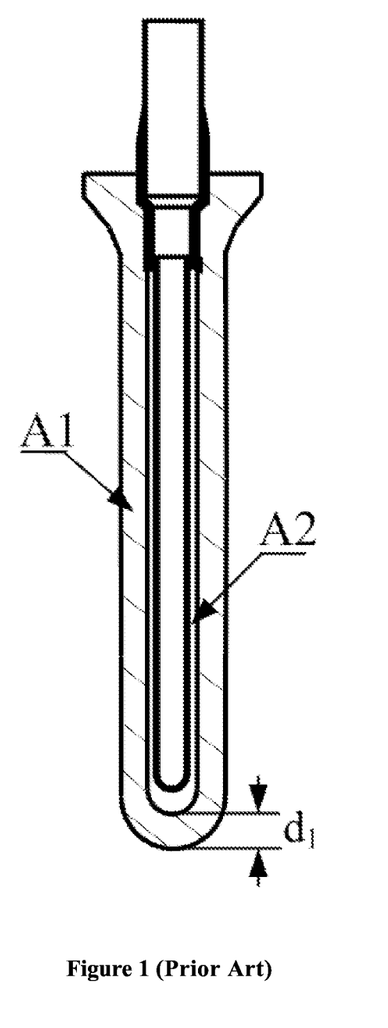
FIG. 1 is a structure diagram of a temperature measuring tube of U.S. Pat. No. 6,846,105B2 in the background art.

According to the heat transfer analysis and the blackbody cavity theory, stable blackbody cavity radiation is realized inside the bottom of the temperature measuring tube with an effective emissivity close to 1 because the structure of the temperature measuring tube and the depth to which the tube is inserted into molten steel are limited to some extent, ensuring the accuracy of radiation temperature measurement. However, the technical solution of the patent is deficient in the slow response speed of temperature measurement. The temperature measuring tube body is composed of two layers inside and outside, in which the outer layer is an aluminum-carbon refractory tube body A1, and the inner layer is a corundum or zirconia tube body A2, as shown in FIG. 1, resulting in slow response. In addition, the outer layer of the aluminium-carbon refractory tube with low strength and high porosity is required to be fabricated into a structure with large wall thickness (wall thickness $d_1$ is about 20 mm-35 mm) and large size to meet the requirements for strength and service life of the temperature measuring tube, which also exacerbates the lag in the temperature response. Therefore, from the insertion into molten steel to the obtaining of the measured temperature, the tube body of this structure takes as long as 5 min-10 min to response, so that the temperature measuring tube is only suitable for tundish temperature measurement at present but can not meet the requirement for quick response of temperature measuring equipment in continuous casting, refining and furnace rotating.

Chinese disclosure Patent Application No. CN102221408A discloses an infrared temperature measuring tube for continuous temperature measurement of molten steel, a component thereof and a preparation method thereof. The inner hole of the temperature measuring tube body disclosed in the patent application is a stepped hole, a heat conducting block is embedded in the larger hole at the lower end of the temperature measuring tube body, and a connecting tube is fixed at the upper end of the temperature measuring tube body. The temperature measuring tube body is made of chrome corundum refractory castable and the heat conducting block is made of aluminum carbon material. Rapid measurement of molten steel temperature is realized through rapid heat transfer of the heat conducting block. The technical solution of the patent is deficient in that immediately after the temperature measuring tube body is inserted into molten steel, the cavity formed by the heat conducting block and the surrounding tube body will be remarkably non-isothermal due to the difference in materials, thermal physical parameters, shapes and sizes, which, together with the uncertainty of the surface emissivity of the heat conducting block, will lead to uncertainty in measurement results and difficulty in ensuring measurement accuracy. In addition, the thickness of the heat conducting block is 20 mm, which will slow the heat transfer. As verified by heat transfer analysis and experiments, it takes about 5 min to response in temperature measurements at this thickness, posing difficulties to achieving the purpose of quick response.

Figure 2:
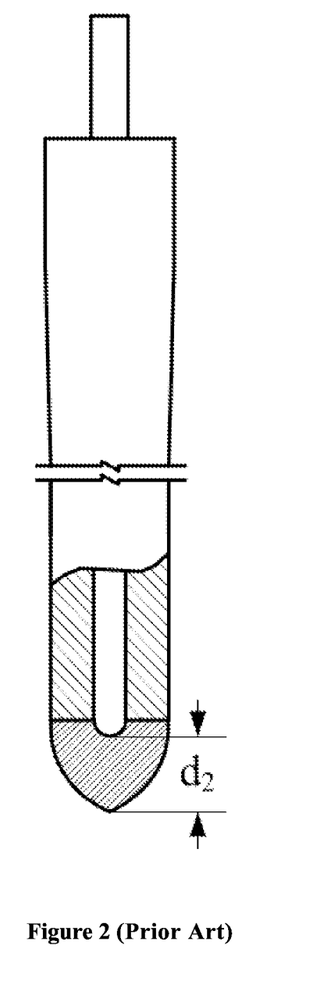
FIG. 2 is a structure diagram of an existing stopper for measuring the temperature of molten steel of Patent CN1936524A in the background art.

The Chinese disclosure Patent Application No. CN1936524A discloses a tundish stopper with continuous temperature measurement function. The stopper with temperature measurement function disclosed in the patent application is a temperature measuring device mounted on an existing stopper. The existing stopper described in the patent is usually made of aluminum carbon, magnesium carbon or zirconium carbon material. As shown in FIG. 2 and as described in the patent, the temperature measuring device is a type S or type B thermocouple, or a radiation temperature measuring device. The technical solution of the patent is deficient in that: in order to resist the strong erosion at the molten steel outlet in the tundish, the existing stopper, which is adopted as the temperature sensing unit, shall have a wall thickness $d_2$ of about 60 mm-100 mm, which will lead to a significant lag in temperature measurement response to an extent of over 20 min as evidenced by heat transfer analysis and experiments, thus the requirements for continuous casting process control is hard to be satisfied.

SUMMARY

The purpose of the disclosure is to provide a temperature measuring device and a temperature measuring method for measuring the temperature of molten metals, aiming to improve the rapidity of continuous temperature measurement of molten metals.

A first aspect of the disclosure provides a temperature measuring device for measuring the temperature of molten metals, comprising a temperature sensing element, a support tube, a connecting tube, and an exhaust structure, wherein the temperature sensing element is a cermet tube with one end closed and the other end open, the wall thickness of the cermet tube is smaller than the wall thickness of the support tube, and the cermet tube can sense the temperature of molten metals and emit stable thermal radiation energy based on the blackbody cavity principle when being extended into the molten metals; the open end of the cermet tube is fixedly connected to one end of the support tube, the cermet tube is communicated with the support tube, and the other end of the support tube is fixedly connected with the connecting tube; the exhaust structure is used to discharge the smoke inside the cermet tube and the support tube.

Optionally, wall thickness d of the cermet tube is 1.0 mm-10.0 mm.

Optionally, $L_1/\Phi_0$ is 1.0 to 20.0, wherein the $L_1$ is a length of a part of the inner cavity of the cermet tube exposed from the support tube and $\Phi_0$ is an inner diameter of the cermet tube.

Optionally, $L_1/\Phi_0$ is 1.0 to 6.0, wherein the $L_1$ is a length of a part of the inner cavity of the cermet tube exposed from the support tube and $\Phi_0$ is an inner diameter of the cermet tube.

Optionally, the cermet tube, the support tube and the connecting tube are coaxial.

Optionally, the material of the cermet tube is a metal-ceramic composite material made of metal powder and ceramic powder by powder metallurgy, comprising at least one of W—$ZrO_2$, Mo—$ZrO_2$, Mo—MgO or W—Mo—$ZrO_2$.

Optionally, the material of the cermet tube comprises a metal having a volume content of 30% to 60%, a fully stabilized zirconia having a volume content of 30% to 60%, and a partially stabilized zirconia having a volume content of 5% to 30%.

Optionally, the outer surface of the cermet tube is provided with an anti-oxidation coating.

Optionally, the support tube has a wall thickness of 15 mm to 100 mm; and/or the support tube has a length of 200 mm to 2200 mm.

Optionally, the exhaust structure comprises a vent pipe and a vent hole, where one end of the vent pipe is arranged in the support tube and communicated with the support tube, the cermet tube and the vent hole, and the other end of the vent pipe is connected with one end of the connecting tube; the other end of the connecting tube is configured to connect with the infrared temperature measuring probe; when measuring the temperature of molten metals, the purge gas blown in from the connecting tube can enter both the cermet tube and the support tube via the vent pipe to blow out the smoke through the gap between the vent pipe and the support tube as well as the vent hole.

Optionally, a distance $L_2$ between an end of the vent pipe adjacent to the cermet tube and an open end of the cermet tube is greater than or equal to 30 mm.

Optionally, the vent hole comprises a through hole on the support tube; and/or, the vent hole comprises a passage composed of a vent groove on the inner wall of the support tube and the outer wall of the connecting tube; and/or, the vent hole comprises a passage composed of a vent groove on the outer wall of the connecting tube and the inner wall of the support tube; and/or, the vent hole comprises a through hole on the connecting tube.

Optionally, the support tube comprises a hollow stopper.

Optionally, the temperature measuring device further comprises an infrared temperature measuring probe and a signal processor; the infrared temperature measuring probe is coaxially connected to the connecting tube and configured to convert the received thermal radiation energy emitted by the cermet tube into an electrical signal, and the signal processor is configured to process the electrical signal and calculate the temperature of molten metals.

A second aspect of the disclosure provides a temperature measuring method for measuring the temperature of a molten metal, wherein the temperature of the molten metal is measured by using the temperature measuring device according to any item of the first aspect of the disclosure and, when the temperature of the molten metal is being measured, the temperature measuring device is inserted into the molten metal to a depth greater than or equal to 8 times the outer diameter of the cermet tube.

For the temperature measuring device and the temperature measuring method for measuring the temperature of a molten metal provided by the disclosure, according to the heat transfer analysis and the blackbody cavity theory, rapid heat transfer and stable blackbody cavity radiation can be realized since the temperature sensing element is a cermet tube whose wall thickness is thinner than the wall thickness of the support tube, thereby enabling a continuous measurement of the temperature of the molten metal with a fast response speed.

Other features of the disclosure and advantages of the features can be understood more clearly from the following detailed description of exemplary embodiments of the disclosure with reference to the accompanying drawings.

BRIEF DESCRIPTION OF THE DRAWINGS

The accompanying drawings, which constitute part of this application, are intended to provide a further understanding of the disclosure. The exemplary embodiments of the disclosure and description thereof serve to explain the disclosure, but do not constitute improper restrictions on the disclosure. In the drawings.

From FIG. 1 to FIG. 10, the marks in the attached drawings represent:

A1—aluminum carbon material tube, A2—corundum or zirconia material tube, 1—cermet tube, 2—support tube, 3—vent tube, 4—connecting tube, 5—vent hole, 6—infrared temperature measuring probe, 7—signal processor, 8—nut, 9—tundish, 10—molten steel.

DESCRIPTION OF THE INVENTION

Together with the Figures in the embodiments of the disclosure, the following text will describe clearly and completely the technical solution implemented in the embodiments of the disclosure. Obviously, the embodiments described are merely part of embodiments implemented in the disclosure, not all embodiments. The following description of at least one exemplary embodiment is in fact illustrative only and is in no way intended to limit the disclosure and its application or use. Based on the embodiments of the disclosure, all other embodiments obtained by those of ordinary skill in the art without making creative work are within the protection scope of the disclosure.

Relative arrangement of components and steps, numerical expressions, and numerical values set forth in these embodiments, unless specifically stated otherwise, should not be explained as a limitation on the present disclosure. It should be understood that the dimensions of the various parts shown in the accompanying drawings are for descriptive purposes and are not necessarily drawn according to the actual scale. Techniques, methods, and apparatus known to those of ordinary skill in the relevant art may not be discussed in detail, but where appropriate, these techniques, methods, and apparatuses should be considered as part of this specification. In all the examples shown and discussed here, any specific value should be interpreted as merely exemplary and not as a limitation. Therefore, other examples of the exemplary embodiments may have different values. It should be noted that similar labels and letters represent similar items in the accompanying drawings below, and therefore, any item already defined in one accompanying drawing does not need to be further discussed in subsequent accompanying drawings.

For ease of description, spatially relative terms, such as "on . . . ", "above . . . ", "on the upper surface of . . . ", and "over", may be used to describe the spatial position relationship between one device or feature and other devices or features as shown in the drawings. It should be understood that the spatially relative terms are intended to include different orientations in use or operation in addition to the orientations described in the drawings. For example, a device described as "above other devices or structures" or "on other devices or structures" will be positioned "below other devices or structures" or "under other devices or structures" if devices illustrated in the drawings are inverted. Thus, the exemplary term "above . . . " can include both "above . . . " and "below . . . ". The device may be otherwise oriented (rotated 90 degrees or at other orientations) and the spatially relative descriptions used herein shall be interpreted accordingly.

As shown in FIGS. 3 to 10, the temperature measuring device for measuring the temperature of a molten metal provided by the disclosure comprises a temperature sensing element, a support tube 2, a connecting tube 4, and an exhaust structure. The temperature sensing element is a cermet tube 1 with one end closed and the other end open; the wall thickness of the cermet tube 1 is smaller than the wall thickness of the support tube 2; the cermet tube 1 is configured to sense the temperature of a molten metal and emit stable thermal radiation energy based on the blackbody cavity principle when being extended into the molten metal. The open end of the cermet tube 1 is fixedly connected to one end of the support tube 2, the cermet tube 1 is communicated with the support tube 2, and the other end of the support tube 2 is fixedly connected with the connecting tube 4. The exhaust structure is configured to discharge the smoke inside the cermet tube 1 and the support tube 2.

The heat transfer speed gets greatly improved as the temperature sensing element of the temperature measuring device is the cermet tube 1 made of a thin-walled cermet material which not only has a better strength and compactness than materials commonly used for temperature measuring devices of molten metals such as aluminum-carbon refractories, magnesium-carbon refractories and zirconium-carbon refractories, but also is excellent in thermal shock resistance and erosion resistance. In the initial stage of inserting the support tube 2 and the cermet tube 1 into a molten metal, the cermet tube 1 is capable of quickly sensing the temperature of the molten metal and emitting stable heat radiation energy to form an online blackbody cavity, thereby enabling a continuous measurement of the temperature of the molten metal with a fast response speed.

Optionally, wall thickness of the cermet tube is 1.0 mm-10.0 mm. For example, wall thickness of the cermet tube 1 may be 1.0 mm, 1.5 mm, 3.0 mm, 5.0 mm, 6.5 mm, 7.0 mm, 8.5 mm, 10.0 mm, etc., which allows the cermet tube to have a small wall thickness, thereby realizing faster sensing of the temperature of molten metals and emitting of stable thermal radiation energy, as well as better continuous measurement of molten metal temperature. Moreover, by appropriately determining the wall thickness range of the cermet tube 1, the temperature measuring performance, the manufacturing cost and the service life of the temperature measuring device can be comprehensively balanced and the overall performance of the temperature measuring device is optimized.

Optionally, $L^1/\Phi_0$ is 1.0 to 20.0, preferably $L_1/\Phi_0$=1.0-6.0. The $L_1$ is a length of a part of the inner cavity of the cermet tube 1 exposed from the support tube 2 and the $\Phi_0$ is an inner diameter of the cermet tube 1. For example, $L_1/\Phi_0$ may be 1, 2, 3, 4.5, 7, 8.5, 10, 12, 15, 17, 18.5, 19, 20, etc.

According to the theoretical calculation and experimental verification, the accuracy of measurement will be ensured in the case that $L_1/\Phi_0$ is greater than or equal to 1.0, that is, the condition of the online blackbody cavity is satisfied, and the effective emissivity of the cavity is close to 1. Appropriate control of the upper limit of the length of part of the cermet tube 1 that is exposed from the support tube 2 is beneficial to controlling the production cost of the temperature measuring device.

Optionally, the cermet tube 1, the support tube 2 and the connecting tube 4 are coaxial. The coaxial connection helps to ensure the alignment of the temperature measuring optical path.

Optionally, the material of the cermet tube 1 is a metal-ceramic composite material made of metal powder and ceramic powder by powder metallurgy, comprising at least one of W—$ZrO_2$, Mo—$ZrO_2$, Mo—MgO or W—Mo—$ZrO_2$. The cermet, which has high strength, compactness, good resistance to corrosion by molten metals and high thermal diffusivity, can be made into thin-walled structure to improve the response speed of the temperature measuring device. The cermet tube 1 is capable of forming the online blackbody cavity in the initial stage of being inserted into molten metals.

Optionally, the material of the cermet tube 1 comprises a metal having a volume content of 30% to 60%, a fully stabilized zirconia having a volume content of 30% to 60%, and a partially stabilized zirconia having a volume content of 5% to 30%.

Optionally, the outer surface of the cermet tube 1 is provided with an anti-oxidation coating which prevents oxidation of the cermet tube 1 during preparation and use.

Optionally, wall thickness of the support tube 2 is 15 mm to 100 mm, and may be, for example, 15 mm, 30 mm, 50 mm, 65 mm, 80 mm, 95 mm, etc.; and/or, length of the support tube 2 is 200 mm to 2200 mm, and may be, for example, 250 mm, 300 mm, 500 mm, 650 mm, 800 mm, 950 mm, 1150 mm, 1300 mm, 1500 mm, 1750 mm, 1800 mm, 1950 mm, 2150 mm, etc.; The support tube 2 has a reasonable wall thickness and/or length to ensure the overall strength and service life of the temperature measuring device and is suitable for measuring temperatures in molten metals of different depths.

The support tube 2 can be made of at least one of the aluminum-carbon refractories, magnesium-carbon refractories, and zirconium-carbon refractories according to actual needs.

The cermet tube 1 and the support tube 2 may be connected in a sealed connection mode according to actual needs. For example, the cermet tube 1 and the support tube 2 may be connected in ways of screw connection, groove-and-protrusion fit connection, conical surface fit connection, or high-temperature binding.

Optionally, the exhaust structure of the temperature measuring device comprises a vent pipe 3 and (a) vent hole(s) 5. One end of the vent pipe 3 is arranged in the support tube 2 and communicated with the support tube 2: the cermet tube 1 and the vent hole(s) 5, and the other end of the vent pipe 2 is connected with one end of the connecting tube 4; and the other end of the connecting tube 4 is configured to coaxially connect with the infrared temperature measuring probe 6. When measuring the temperature of a molten metal, the purge gas blows in from the connecting tube 4 and enters both the support tube 2 and the cermet tube 1 via the vent pipe 3 and, after which, blows away the smoke inside the cermet tube 1 and the support tube 2 through the gap between the vent pipe 3 and the support tube 2 as well as the vent hole(s) 5. When the temperature measuring device measures the temperature, the smoke can be blown away from the temperature measuring optical path by blowing the purge gas (e.g. compressed air, preferably inert gas $N_2$ or Ar) into the connecting tube 4 and letting the purge gas enter through the vent pipe 3, and then be discharged to the outside of the temperature measuring device through the vent hole(s) 5, allowing the radiation temperature measuring device to measure temperatures more accurately.

Optionally, a distance $L_2$ between the end of the vent pipe 3 adjacent to the cermet tube 1 and the open end of the cermet tube 1 is greater than or equal to 30 mm. The reasonable location of the vent pipe 3 allows the smoke to be effectively discharged from the temperature measuring optical path and improves the accuracy of the temperature measuring device.

The vent hole(s) 5 may be arranged in a variety of ways. For example, the vent hole(s) 5 comprise(s) a through-hole on the support tube 2; and/or, the vent hole(s) 5 comprise(s) a passage formed by a vent groove on the inner wall of the support tube 2 and the outer wall of the connecting tube 4, in which the vent groove is optionally arranged along the axial direction; and/or, the vent hole(s) 5 comprise(s) a passage formed by a vent groove on the outer wall of the connecting tube 4 and the inner wall of the support tube 2, in which the vent groove is optionally arranged along the axial direction; and/or, the vent hole(s) 5 comprise(s) a through-hole on the connecting tube 4.

The number of the vent hole(s) 5 may be determined according to the flow rate of the smoke, the size of the temperature measuring device, etc., and may be 1, 2, 3, 4, 5, 6, 7, 8, 10, 11, 12, etc.

How to connect the connecting tube 4 and the support tube 2 may be determined according to actual needs. For example, the support tube 2 and the connecting tube 4 can be connected by means of conical surface fit connection and pin positioning; or the support tube 2 and the connecting tube 4 can be connected by means of cylindrical surface fit connection and pin positioning; alternatively, the support tube 2 and the connecting tube 4 may be connected by threading, with the support tube 2 internally embedded into a nut 8 and the connecting tube 4 fitted with the thread of the nut 8.

How to connect the connecting tube 4 and the vent pipe 3 may be determined according to actual needs. For example, the connecting tube 4 and the vent pipe 3 can be connected by means of high temperature binder bonding and pin positioning.

Optionally, the support tube 2 is a hollow stopper. The temperature measuring device with the stopper as the support tube 2 and the cermet tube 1 as the temperature sensing element has two advantages: one is that the temperature measured by the device is closer to the temperature of molten steel in a crystallizer than the temperature measured by the existing temperature measuring device, and is more referential for solidification control of molten steel in the continuous casting process; besides, the thin-walled structure of the cermet tube 1 of the temperature sensing element enables the temperature measuring device of the present embodiment to have a faster temperature measuring response speed, within about 90 seconds to be specific, thus meeting the requirements of continuous casting process control. If the existing stopper made of aluminum carbon or magnesium carbon is used for the temperature measuring device, the bottom that senses the temperature shall have a wall thickness of 60 mm-100 mm to resist the strong scouring at the molten steel outlet of the tundish, which will cause such a significant lag in temperature measuring response that, according to theoretical analysis and experimental tests, the temperature response time will be about more than 20 min, failing to meet the requirement of continuous casting process control. Therefore, it is not feasible. In addition, the temperature measuring device which also functions as one stopper has dual functions of measuring the temperature of molten steel and controlling flow rate of molten steel, and costs less than using one temperature measuring device and one stopper separately.

Optionally, the temperature measuring device further comprises an infrared temperature measuring probe 6 and a signal processor 7, in which the infrared temperature measuring probe 6 is coaxially connected to the connecting tube 4 and configured to convert the received thermal radiation energy emitted by the cermet tube 1 into an electrical signal, and the signal processor is configured to process the electrical signal and calculate the temperature of molten metals.

The disclosure also provides a temperature measurement method for measuring the temperature of molten metals, which comprises measuring the temperature of molten metals by using the said temperature measuring device.

Optionally, when the temperature of a molten metal is being measured, the temperature measuring device is inserted into the molten metal to a depth greater than or equal to 8 times the outer diameter of the cermet tube 1. By limiting the insertion depth as described above, stable blackbody cavity radiation can be achieved, thus ensuring the accuracy of temperature measurement.

Optionally, the temperature measurement method comprises blowing in the smoke purge gas from the connecting tube 4 and letting the gas into and through the vent pipe 3 to blow the smoke though the gap between the vent pipe 3 and the support tube 2 and then out of the device via the vent hole(s) 5. The purge gas is capable of eliminating the smoke volatilized when the support tube 2 is at a high temperature, thereby preventing the smoke from interfering with the radiation temperature measurement.

The temperature measurement method of the disclosure for measuring the temperature of molten metals has all the advantages of the said temperature measuring device.

The following is a detailed description of embodiments of the disclosure in combination with the attached drawings.

FIRST EMBODIMENT

Figure 3:
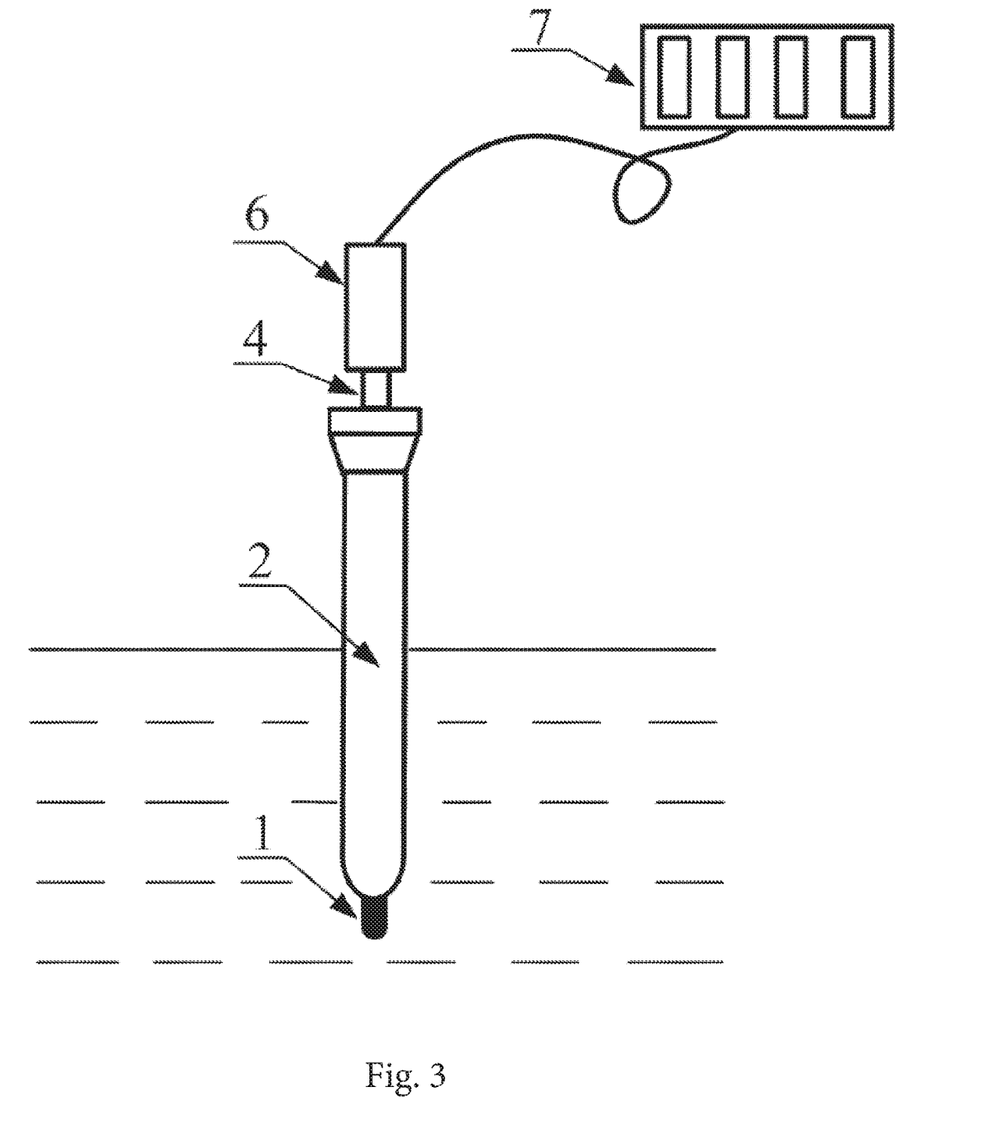
FIG. 3 is a structure diagram of a temperature measuring device which is in a measuring state for measuring the temperature of a molten metal according to a First Embodiment of the disclosure.
Figure 4:
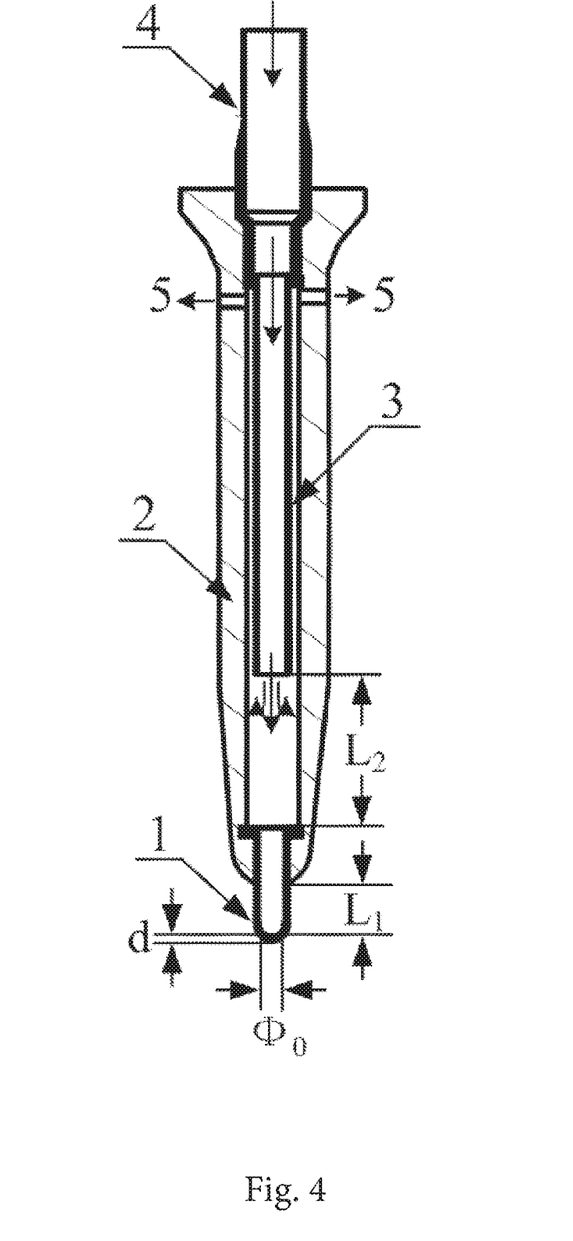
FIG. 4 is a structure diagram of a measuring body of a temperature measuring device for measuring the temperature of a molten metal according to a First Embodiment of the disclosure.

FIG. 3 and FIG. 4 illustrate the structure of a temperature measuring device according to a First Embodiment of the disclosure which may be applied to continuously and quickly measure the temperature of molten steel in a tundish.

As shown in FIG. 3 and FIG. 4, the temperature measuring device comprises a measuring body, an infrared temperature measuring probe 6 and a signal processor 7.

The measuring body comprises a cermet tube 1 as a temperature sensing element, a support tube 2, a connecting tube 4 and an exhaust structure which comprises a vent pipe 3 and vent holes 5.

The top end of the cermet tube 1 is an open end and the bottom end is a closed end. The cermet tube 1 has a cavity. The open end of the cermet tube 1 is connected to the bottom end of the support tube 2. The cermet tube 1 can sense the temperature of molten metals and emit stable thermal radiation energy based on the blackbody cavity principle when being extended into the molten metals.

The infrared temperature measuring probe 6 receives thermal radiation from the cavity of the cermet tube 1 and converts the received thermal radiation energy into an electrical signal. The signal processor 7 processes the electrical signal and calculates the temperature of the molten metal into which the cermet tube 1 of the temperature measuring device is inserted.

In the present embodiment, the cermet tube 1 has a wall thickness of 2.5 mm and an inner diameter of 22.5 mm By appropriately determining the wall thickness range of the cermet tube 1, the temperature measuring performance, the manufacturing cost and the service life of the temperature measuring device can be comprehensively balanced and the overall performance of the temperature measuring device is optimized.

By virtue of the thinner wall thickness and better thermal conductivity than the temperature measuring tube commonly seen, the cermet tube 1 is capable of quickly forming an online blackbody cavity in the initial stage of being inserted into molten metals for fast response.

As shown in FIG. 4, the open end of the cermet tube 1 is embedded in the bottom end of the support tube 2 and forms a sealing connection with the bottom end of the support tube 2. The cermet tube 1 is coaxially connected with the support tube 2. In the present embodiment, the two are connected by grooves and bosses, which effectively ensures the coaxiality and the axial position of the cermet tube 1 and the support tube 2.

In the present embodiment, the open end of the cermet tube 1 is embedded in the bottom end of the support tube 2, where the embedded part has a length of 50 mm and the unembedded part has a length of 100 mm.

The length of the embedded part ensures a strong coaxial connection between the cermet tube 1 and the support tube 2, and helps control the production cost of the temperature measuring device. The length of the unembedded part satisfies the condition of forming the blackbody cavity, and the effective emissivity of the cavity is close to 1, thereby ensuring measurement accuracy and facilitating control of the production cost of the temperature measuring device.

Preferably, the cermet tube 1 is made of a cermet material with high thermal conductivity, resistant to molten steel corrosion and scouring, high strength and compactness. In the present embodiment, the cermet material is Mo—$ZrO_2$ The cermet material forming the cermet tube 1 has a metal phase volume content of 50%, a partially stabilized zirconia volume content of 15%, and a stabilized zirconia volume content of 35%.

Cermet materials, which not only have high strength, compactness and good resistance to the erosion by molten metals but also have excellent thermal conductivity, help to improve the response speed of the temperature measuring device. In the early stage when the measuring body is inserted into molten metals, the cermet tube 1 is capable of quickly forming the online blackbody cavity.

In the present embodiment, outer surfaces of the cermet tube 1 and the support tube 2 are coated with anti-oxidation coatings which prevent high temperature oxidation during the preparation and use of the measuring body.

In the present embodiment, the top of the support tube 2 and the infrared temperature measuring probe 6 are coaxially connected with the connecting tube 4. The infrared temperature measuring probe 6 comprises an optical fiber infrared temperature measuring probe which is connected with the connecting tube 4, specifically, in a manner of conical surface fit connection. The infrared temperature measuring probe 6 is connected above the connecting tube 4.

As shown in FIG. 4, the support tube 2 and the connecting tube 4 are coaxially connected in a threaded manner. Specifically, the support tube 2 is internally embedded into a nut 8, and the connecting tube 4 is fitted with the thread of the nut 8.

The support tube 2 is made of an aluminum-carbon refractory with high temperature resistance, slag penetration resistance and oxidation resistance.

During measuring, the cermet tube 1 is capable of quickly forming the blackbody cavity under the support of the support tube 2 due to the rapid heat transfer characteristics of the cermet tube 1 and the advantages of the material of the support tube 2 in terms of low cost and good resistance to slag and molten metal erosion, thus, the rapid temperature measurement of molten metals can be realized.

In addition, the support tube 2 only acts to carry the cermet tube 1 and does not participate in the formation of the blackbody cavity used to measure the temperature of a molten metal if the cermet tube 1 is embedded in the support tube 2 made of low-cost refractory material and then extended into the molten metal, cermet materials are more expensive than refractory materials commonly used for manufacturing temperature measuring tubes, so the cost of a temperature measuring device is lower.

In the present embodiment, the support tube 2 has a wall thickness of 25 mm and a length of 800 mm. The support tube 2 has a reasonable wall thickness and/or length to ensure the overall strength and service life of the temperature measuring device and is suitable for measuring temperatures in molten metals of different depths.

In the present embodiment, the vent pipe 3 is made of alumina and is communicated with the cavity of cermet tube 1. The vent pipe 3 is made of alumina, which allows the vent pipe 3 to withstand high temperature, makes the vent pipe 3 suitable for the working environment of the temperature measuring device, and extends the service life of the temperature measuring device.

As shown in FIG. 4, the vent pipe 3 is arranged in the support tube 2 with a 2 mm gap between the two, which forms a fluid channel for blowing smoke.

The vent holes 5 are communicated with the outside. As shown in FIG. 4, the vent holes 5 according to the First Embodiment are through holes on the support tube 2. The number of the vent holes 5 is 2.

When the temperature measuring device measures temperature, the purge gas is blown into the connecting tube 4, into the vent pipe 3 through connecting tube 4, and into the inside of both the support tube 2 and cermet tube 1 through the vent pipe 3 to blow away the smoke on the temperature measuring optical path, and then is discharged out of the temperature measuring device via the vent holes 5 after passing through the gap between the vent pipe 3 and the support tube 2, which ensures that the optical path is clean and allows the temperature measuring device to measure the temperature more accurately.

For the vent pipe 3, one end is connected to the connecting tube 4 and a distance $L_2$ between the end adjacent to the cermet tube 1 and the open end of the cermet tube 1 is greater than or equal to 30 mm, which allows the end of the vent pipe 3 adjacent to the cermet tube 1 to be located below the molten metal level and at a certain distance above the open end of the cermet tube 1, for example, 100 mm, while the temperature measuring device is making measurements. Reasonable location of the vent pipe 3 can promote the effective discharge of smoke from the temperature measuring optical path, ensure the cleanliness of the temperature measuring optical path, and improve the accuracy of measurement.

The connecting tube 4 is connected with the vent pipe 3 in a way that may be determined as needed. In the present embodiment, the connecting tube 4 and the vent pipe 3 can be connected by means of high temperature binder bonding and pin positioning.

The following briefly describes the process by which the temperature measuring device according to the First Embodiment measures the temperature of molten steels.

Insert the measuring body end which is provided with the cermet tube 1 into a molten metal to a depth which is 10 times the outer diameter of the cermet tube 1 in the present embodiment.

In other embodiments, the measuring body is inserted into a molten metal to a depth greater than or equal to 8 times the outer diameter of the cermet tube 1. According to heat transfer analysis and blackbody cavity radiation theory, stable blackbody cavity radiation can be achieved by limiting the insertion depth as described above, thus ensuring the accuracy of temperature measurement.

The temperature measuring device can be fixed on the tray on the cover of the tundish. The connecting tube 4 is connected with the infrared temperature measuring probe 6, and the infrared temperature measuring probe 6 is connected with the signal processor 7. After thermal equilibrium is achieved between the cermet tube 1 and a molten metal, the cavity of the cermet tube 1 is formed into the online blackbody cavity, the infrared temperature measuring probe 6 receives thermal radiation energy from the blackbody cavity and converts the thermal radiation energy into an electrical signal, and the signal processor 7 receives the electrical signal and calculates the molten metal temperature according to the electrical signal.

In addition, the purge gas blows in from the connecting tube 4 and then flows into the vent pipe 3. The purge gas flowing from the vent pipe 3 causes the smoke on the temperature measuring optical path to flow through the gap between the vent pipe 3 and the support tube 2 to the vent hole 5 and then be blown out to the outside of the temperature measuring device from the vent holes 5.

In the present embodiment, the purge gas is $N_2$. In other embodiments, the purge gas may be another type of gas, such as compressed air, or preferably another inert gas, such as Ar. The purge gas is capable of eliminating the smoke volatilized when the support tube 2 is at a high temperature, thereby preventing the smoke from interfering with the radiation temperature measurement.

According to the experimental results, in terms of temperature measurement accuracy, the error in temperature measurement achieved by the temperature measuring device of the First Embodiment is ±3° C. compared with the error achieved by the second-class B platinum-rhodium thermocouple, and the response time of the temperature measuring device can be as less as 60s.

For the part not specified in the First Embodiment, the relevant contents of the remaining embodiments can be referred to.

SECOND EMBODIMENT

Figure 5:
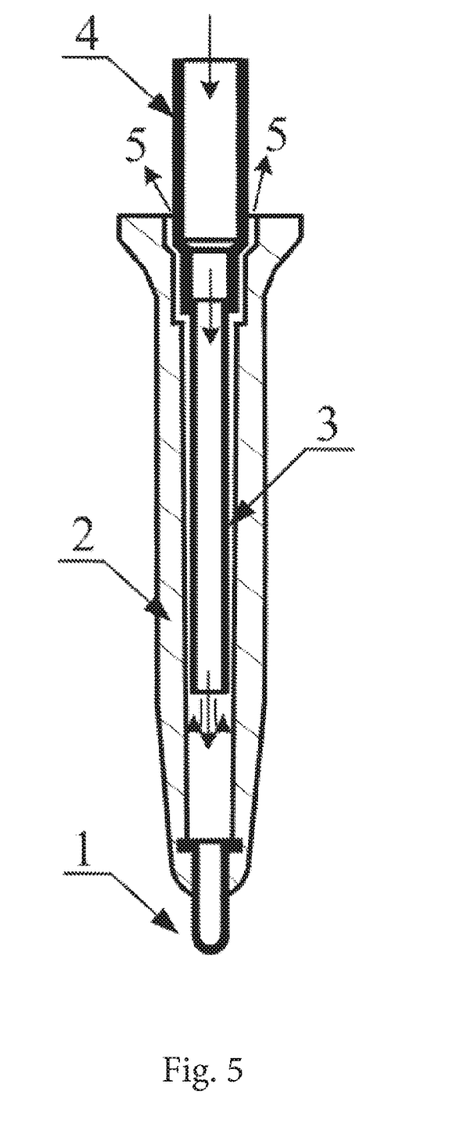
FIG. 5 is a structure diagram of a measuring body of a temperature measuring device for measuring the temperature of a molten metal according to a Second Embodiment of the disclosure.
Figure 6:
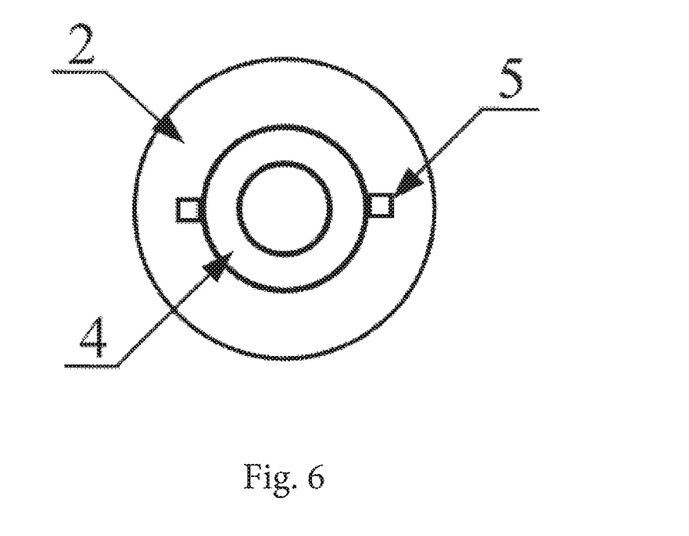
FIG. 6 is a structure diagram of vent holes of the measuring body of the temperature measuring device shown in FIG. 5.

FIG. 5 is a structure diagram of a measuring body of a temperature measuring device for measuring the temperature of a molten metal according to a Second Embodiment of the disclosure. FIG. 6 is a structure diagram of vent holes of the temperature measuring device shown in FIG. 5.

As shown in FIG. 5 and FIG. 6, the present embodiment is different from the First Embodiment in that the vent holes 5 are composed of two vent grooves along the axis of the inner wall of the support tube 2 and the outer wall of the connecting tube 4. The number of the vent grooves is 2. In addition, the top of the support tube 2 and the connecting tube 4 is connected by means of cylindrical surface fit connection and pin positioning.

For the part not specified in the Second Embodiment, the relevant contents of the remaining embodiments can be referred to.

THIRD EMBODIMENT

Figure 7:
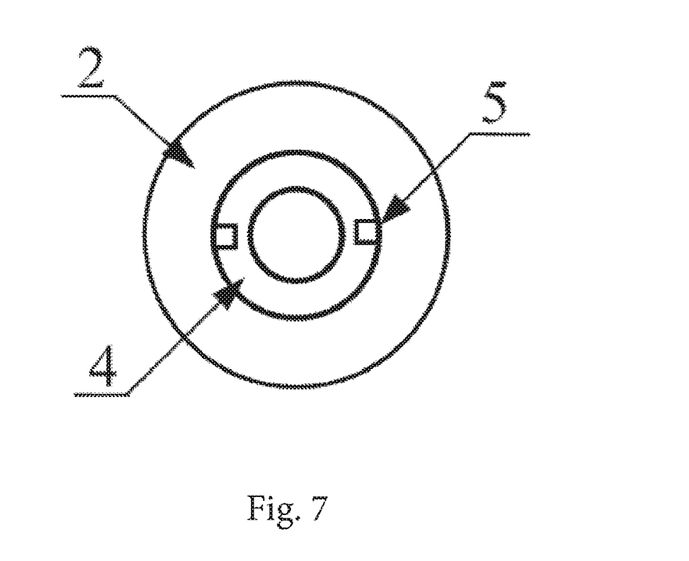
FIG. 7 is a structure diagram of vent holes of a measuring body of a temperature measuring device for measuring the temperature of a molten metal according to a Third Embodiment of the disclosure.

FIG. 7 is a structure diagram of vent holes of a measuring body of a temperature measuring device for measuring the temperature of a molten metal according to a Third Embodiment of the disclosure.

As shown in FIG. 7, the Third Embodiment is different from the First Embodiment in that the vent holes 5 are composed of two vent grooves along the axis of the outer wall of the connecting tube 2 and the inner wall of the support tube 4. The number of the vent grooves is 2.

For the part not specified in the Third Embodiment, the relevant contents of the remaining embodiments can be referred to.

FOURTH EMBODIMENT

Figure 8:
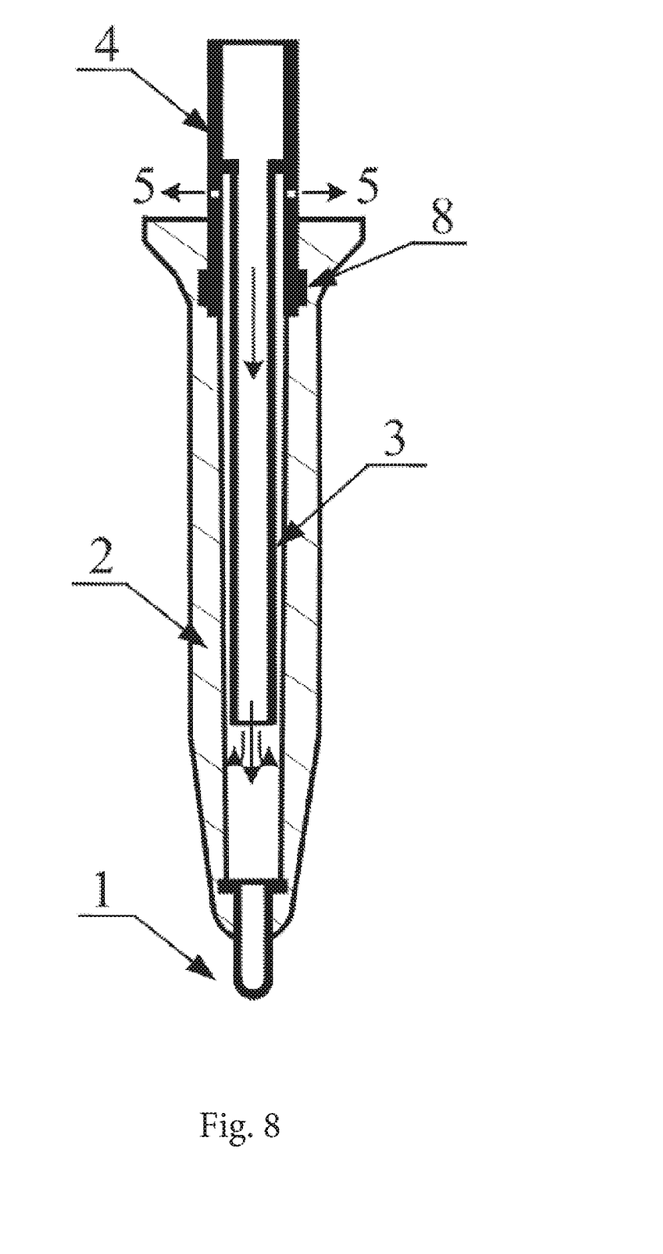
FIG. 8 is a structure diagram of a measuring body of a temperature measuring device for measuring the temperature of a molten metal according to a Fourth Embodiment of the disclosure.

FIG. 8 is a structure diagram of a measuring body of a temperature measuring device for measuring the temperature of a molten metal according to a Fourth Embodiment of the disclosure.

As shown in FIG. 8, the Fourth Embodiment is different from the First Embodiment in that the vent holes 5 are through holes on the connecting tube 4, and the through holes are 2 in quantity.

For the part not specified in the Fourth Embodiment, the relevant contents of the remaining embodiments can be referred to.

FIFTH EMBODIMENT

Figure 9:
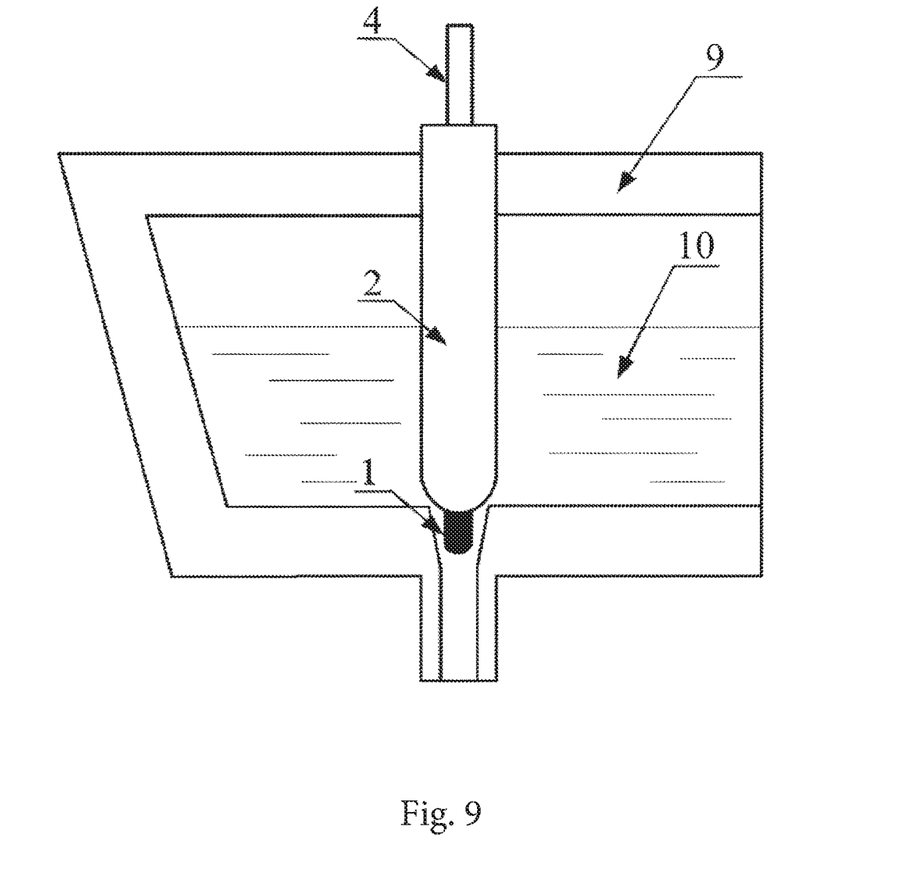
FIG. 9 is a structure diagram of a temperature measuring device which is in a measuring state for measuring the temperature of a molten metal according to a Fifth Embodiment of the disclosure.
Figure 10:
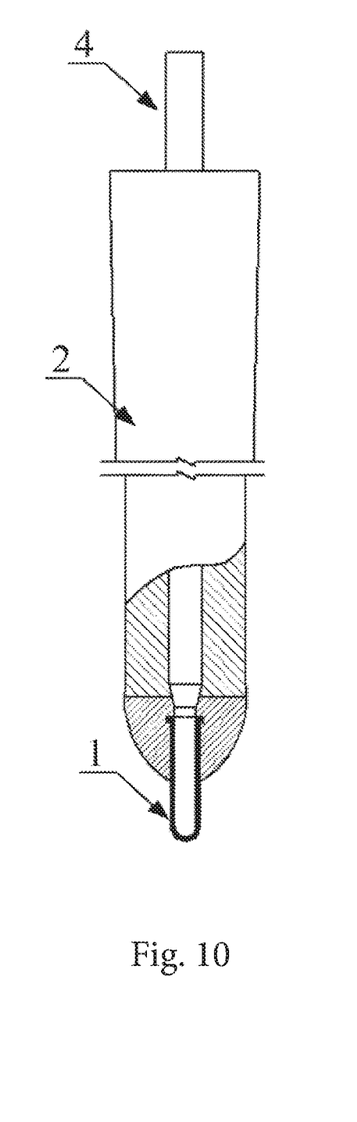
FIG. 10 is a structure diagram of a measuring body of a temperature measuring device for measuring the temperature of a molten metal according to a Fifth Embodiment of the disclosure.

FIG. 9 is a structure diagram of a temperature measuring device which is in a measuring state for measuring the temperature of a molten metal according to a Fifth Embodiment of the disclosure. FIG. 10 is a schematic diagram of a measuring body of a temperature measuring device according to the Fifth Embodiment of the disclosure.

As shown in FIGS. 9 and 10, the Fifth Embodiment is different from the First Embodiment in that, the stopper is used, the cermet tube 1 is mounted at the bottom of the stopper which works as the support tube 2, and the stopper may function as the support tube 2 of the measuring body to realize the function of temperature measurement.

The stopper is a rod body arranged at the outlet of molten metal in the tundish 9 to control the outflow speed of molten metals such as molten steel 10. The temperature measured by the temperature measuring device which also works as one stopper is closer to the temperature of molten steel in a crystallizer (not shown) than the temperature measured by the existing temperature measuring tube, and is more referential for solidification control of molten steel in the continuous casting process. In addition, the temperature measuring device which also functions as a stopper serving the dual functions of measuring the temperature of molten steel and controlling flow rate of molten steel, and costs less than using one temperature measuring device and one stopper separately.

For the part not specified in the Fifth Embodiment, the relevant contents of the remaining embodiments can be referred to.

The above embodiments of the disclosure are capable of measuring the temperature of molten metals so rapidly and continuously that the response time can be reduced from 5-10 min taken by the existing temperature measuring device made of aluminum carbon or magnesium carbon to within 90 seconds, and can be used to measure the temperature of a continuous casting tundish in the whole process, especially in the process of continuous casting and ladle changing with rapid response to temperature measurement. In addition, these embodiments can also be applied to continuous temperature measurement in situations where molten steel temperature changes rapidly, such as secondary refining, and continuous measurement of other high temperature melts. The stopper may be employed meanwhile to measure temperature.

Finally, it is noted that the above embodiments are only used to explain the technical solution of the disclosure and shall not be construed as a limitation. Although the disclosure is described in detail with reference to preferred embodiments, those of ordinary skill in the art should understand: the specific embodiment of the disclosure may still be modified or some technical features may be replaced by equivalent without breaking away from the spirit of the technical solution of the disclosure, and all modified embodiments and replaced technical features shall be covered by technical solution of this disclosure patent.

The invention claimed is:

1. A temperature measuring device for measuring the temperature of molten metals, comprising:
   a cermet tube,
   a support tube,
   a connecting tube,
   an exhaust structure,
   wherein the cermet tube is provided with a closed end and an open end, the wall thickness of the cermet tube is smaller than the wall thickness of the support tube, and the cermet tube is configured to sense the temperature of molten metals and emit stable thermal radiation energy based on the blackbody cavity principle when being extended into the molten metals;
   the open end of the cermet tube is fixedly connected to one end of the support tube, the cermet tube is communicated with the support tube, and the other end of the support tube is fixedly connected with the connecting tube;
   the exhaust structure is configured to discharge the smoke inside the cermet tube and the support tube and comprises a vent pipe and a vent hole, wherein one end of the vent pipe is arranged in the support tube and communicated with the support tube, the cermet tube, and the vent hole, and the other end of the vent pipe is connected with one end of the connecting tube, and wherein when measuring the temperature of molten metals, purge gas blown in from the connecting tube enter both the cermet tube and the support tube via the vent pipe to blow out the smoke through the gap between the vent pipe and the support tube as well as the vent hole; and
   wherein the support tube comprises a hollow stopper, the stopper is a rod body configured to arrange at an outlet of molten metal in a tundish to control the outflow speed of molten metals, and the cermet tube is mounted at the bottom of the stopper.

2. The temperature measuring device as claimed in claim 1, wherein the wall thickness d of the cermet tube is 1.0 mm to 10.0 mm.

3. The temperature measuring device as claimed in claim 1, wherein $L1/\Phi_0$ is 1.0 to 20.0, wherein the L1 is a length of a part of the inner cavity of the cermet tube exposed from the support tube and the $\Phi 0$ is an inner diameter of the cermet tube.

4. The temperature measuring device as claimed in claim 1, wherein $L1/\Phi_0$ is 1.0 to 6.0, wherein the L1 is a length of a part of the inner cavity of the cermet tube exposed from the support tube and the $\Phi 0$ is an inner diameter of the cermet tube.

5. The temperature measuring device as claimed in claim 1, wherein the cermet tube, the support tube and the connecting tube are coaxial.

6. The temperature measuring device as claimed in claim 1, wherein the material of the cermet tube is a metal-ceramic composite material made of metal powder and ceramic powder by powder metallurgy, comprising at least one of W—ZrO2, Mo—ZrO2, Mo—MgO or W—Mo—ZrO2.

7. The temperature measuring device as claimed in claim 1, wherein the material of the cermet tube comprises a metal having a volume content of 30% to 60%, a fully stabilized zirconia having a volume content of 30% to 60%, and a partially stabilized zirconia having a volume content of 5% to 30%.

8. The temperature measuring device as claimed in claim 1, wherein the outer surface of the cermet tube is provided with an anti-oxidation coating.

9. The temperature measuring device as claimed in claim 1, wherein the support tube has at least one of a wall thickness of 15 mm to 100 mm or a length of 200 mm to 2200 mm.

10. The temperature measuring device as claimed in claim 1, wherein the other end of the connecting tube is configured to connect with an infrared temperature measuring probe.

11. The temperature measuring device as claimed in claim 10, wherein a distance L2 between an end of the vent pipe adjacent to the cermet tube and the open end of the cermet tube is greater than or equal to 30 mm.

12. The temperature measuring device as claimed in claim 10, wherein the vent hole comprises at least one of a through hole on the support tube, a passage composed of a vent groove on the inner wall of the support tube and the outer wall of the connecting tube, a passage composed of a vent groove on the outer wall of the connecting tube and the inner wall of the support tube, or a through hole on the connecting tube.

13. The temperature measuring device as claimed in claim 1, wherein the temperature measuring device further comprises an infrared temperature measuring probe and a signal processor, wherein the infrared temperature measuring probe is coaxially connected to the connecting tube and configured to convert the received thermal radiation energy emitted by the cermet tube into an electrical signal, and the signal processor is configured to process the electrical signal and calculate the temperature of molten metals.

14. A temperature measuring method for measuring the temperature of a molten metal, wherein the temperature of the molten metals is measured by using the temperature measuring device according to claim 1 and, when the temperature of the molten metal is being measured, the temperature measuring device is inserted into the molten metals to a depth greater than or equal to 8 times the outer diameter of the cermet tube.

* * * * *